(12) United States Patent
Beatty et al.

(10) Patent No.: US 11,464,704 B2
(45) Date of Patent: Oct. 11, 2022

(54) CRYOTHERAPEUTIC DELIVERY DEVICE

(71) Applicant: Boston Scientific Scimed inc., Maple Grove, MN (US)

(72) Inventors: Aideen B. Beatty, Galway (IE); Martin L. Fawdry, Galway (IE); Peter M. McKenna, County Antrim (IE); Sophie A. Gannon, Galway (IE); Sara J. Callagy, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1007 days.

(21) Appl. No.: 16/036,377

(22) Filed: Jul. 16, 2018

(65) Prior Publication Data

US 2019/0015298 A1    Jan. 17, 2019

Related U.S. Application Data

(60) Provisional application No. 62/533,656, filed on Jul. 17, 2017.

(51) Int. Cl.
*A61J 1/14* (2006.01)
*A01N 1/02* (2006.01)
(Continued)

(52) U.S. Cl.
CPC .......... *A61J 1/1443* (2013.01); *A01N 1/0221* (2013.01); *A01N 1/0263* (2013.01); *A61J 1/2096* (2013.01);
(Continued)

(58) Field of Classification Search
CPC ...... A61J 1/1443; A61J 1/1456; A61J 1/2096; A61J 1/05; A61M 1/0281; A61M 1/67;
(Continued)

(56) References Cited

U.S. PATENT DOCUMENTS 5,779,668 A * 7/1998 Grabenkort ......... A61M 5/3129
604/191
2003/0069543 A1* 4/2003 Carpenter ......... A61M 25/0084
604/190
(Continued)

FOREIGN PATENT DOCUMENTS

| CN | 104519976 A | 4/2015 |
| CN | 104704106 A | 6/2015 |

(Continued)

OTHER PUBLICATIONS

International Search Report and Written Opinion issued in PCT/US2018/042258, dated Sep. 27, 2018, 14 pages.

*Primary Examiner* — Ariana Zimbouski
(74) *Attorney, Agent, or Firm* — Seager, Tufte & Wickhem LLP

(57) ABSTRACT

A device for aseptic delivery of biological material from a vial includes a tubular barrel, a filter assembly, and a dispersion funnel assembly. The tubular barrel includes a receiving end to accept at least a portion of the vial within the tubular barrel, and a dispensing end opposite the receiving end. The filter assembly is fluidly connected to the dispensing end of the tubular barrel. The dispersion funnel assembly is configured to connect to the vial, and to be disposed at least partially within the tubular barrel. The dispersion funnel assembly has an open configuration to disperse the biological material from the vial into the tubular barrel between the dispersion funnel assembly and the filter assembly, and a closed configuration to force the dispersed biological material through the filter assembly when the dispersion funnel assembly is moved toward the dispensing end of the tubular barrel.

12 Claims, 13 Drawing Sheets

(51) Int. Cl.
 *A61J 1/20* (2006.01)
 *A61M 1/02* (2006.01)
 *A61M 5/178* (2006.01)

(52) U.S. Cl.
 CPC ........... *A61M 1/0281* (2013.01); *A61M 5/178* (2013.01); *A61M 2202/0437* (2013.01)

(58) Field of Classification Search
 CPC ...... A61M 2202/0437; A61M 2202/08; A61M 5/178; A61M 5/3145; A01N 1/0263; A01N 1/0221; B01D 29/085
 See application file for complete search history.

(56) References Cited

U.S. PATENT DOCUMENTS

2006/0178644 A1   8/2006  Reynolds
2016/0008808 A1   1/2016  Levine et al.

FOREIGN PATENT DOCUMENTS

| EP | 0821599 A1 | 2/1998 |
|---|---|---|
| JP | H10337321 A | 12/1998 |
| WO | 2014080430 A1 | 5/2014 |

\* cited by examiner

CRYOTHERAPEUTIC DELIVERY DEVICE

CROSS-REFERENCE TO RELATED APPLICATION

This application claims priority to Provisional Application No. 62/533,656, filed Jul. 17, 2017, which is herein incorporated by reference in its entirety.

TECHNICAL FIELD

The present invention relates to systems, devices, and methods for the storage and delivery of biological material to a patient. More specifically, the invention relates to systems, devices, and methods for the storage and delivery of cryotherapeutic biological material to a patient.

BACKGROUND

Biological materials for cellular therapy, such as allogenic or autologous transplant cells, are typically produced by aspirating stem cells from a donor or patient, respectively, and then isolating and differentiating the stem cells. The differentiated stem cells are then expanded to produce a quantity of the differentiated stem cells sufficient for the cellular therapy. Prior to storage, the differentiated stem cells are washed and suspended in a solution including proteins and a cryoprotectant, such as dimethylsulfoxide (DMSO). The suspended cells are then transferred to bags or vials and frozen with liquid nitrogen at a slow, controlled rate.

The frozen suspended cells are transferred to a clinic and remain frozen until ready for use. The cells are thawed in the bags, and then transferred from the bags to specialized equipment for washing. The washing removes the cryoprotectant which can increase some side effects of the cellular therapy if not removed. In some cases, the equipment must be operated by specially trained professionals using specialized reagents. The use of the specialized equipment, professionals, and reagents is costly. In other cases, the equipment can use inexpensive saline solution instead of the specialized reagents, but requires centrifugation of the cells. The centrifugation can damage the cells and cause them to clump together, reducing the viability of the cells and the effectiveness of the cell therapy.

Once the transplant cells are washed of the cryoprotectant, they are transferred from the specialized equipment to a syringe or catheter for delivery to the patient. Each of the transfer steps, such as from bag to washing equipment and from the washing equipment to a syringe, exposes the cells to the atmosphere and introduces an increased risk of contamination and infection, especially in high-risk, immune-compromised patients.

SUMMARY

Example 1 is a device for aseptic delivery of biological material from a vial. The device includes a tubular barrel, a filter assembly, and a dispersion funnel assembly. The tubular barrel includes a receiving end to accept at least a portion of the vial within the tubular barrel, and a dispensing end opposite the receiving end. The filter assembly is fluidly connected to the dispensing end of the tubular barrel. The dispersion funnel assembly is configured to connect to the vial, and to be at least partially disposed within the tubular barrel. The dispersion funnel assembly has an open configuration to disperse the biological material from the vial into the tubular barrel between the dispersion funnel assembly and the filter assembly, and a closed configuration to force the dispersed biological material through the filter assembly when the dispersion funnel assembly is moved toward the dispensing end of the tubular barrel.

Example 2 is the device of Example 1, wherein the filter assembly includes a filter medium, the filter assembly selectable between an open state wherein the filter medium prevents the biological material from passing through the filter assembly but permits liquid to pass through the filter assembly, a bypass state wherein the biological material can pass through the filter assembly to deliver the biological material, and, optionally, a closed state wherein no liquid or biological material can pass through the filter assembly.

Example 3 is the device of Example 2, wherein the filter assembly is only selectable from the closed state to the open state and from the open state to the bypass state.

Example 4 is the device of Example 2, wherein the filter assembly further includes a first output port and a second output port. The first output port is in fluid communication with the dispensing end of the tubular barrel when the filter assembly is in the open state. The second output port is in fluid communication with the dispensing end of the tubular barrel when the filter assembly is in the bypass state.

Example 5 is the device of any of Examples 1-4, wherein the dispersion funnel assembly includes an inner funnel, an outer funnel, and a compressible seal. The inner funnel includes a first plurality of openings through the inner funnel. The outer funnel includes a second plurality of openings through the outer funnel. The inner funnel is coaxial with and nested within the outer funnel such that the first plurality of openings is aligned with the second plurality of openings. The compressible seal is disposed between the inner funnel and the outer funnel. In the open configuration, the compressible seal permits a fluid connection between the inner funnel and the outer funnel. In the closed configuration, the compressible seal is compressed between the inner funnel and the outer funnel to prevent the fluid connection between the inner funnel and the outer funnel.

Example 6 is the device of Example 5, wherein the inner funnel further includes a first tubular portion and a first conical portion coaxial with and projecting away from the first tubular portion. The first conical portion defines a first opening angle and the first plurality of openings. The outer funnel further includes a second tubular portion a second conical portion coaxial with and projecting away from the second tubular portion. The second conical portion defines a second opening angle and the second plurality of openings. The second opening angle substantially equal to the first opening angle.

Example 7 is the device of either of Examples 5 or 6, further including a dispersion funnel retaining device configured to engage a portion of the outer funnel extending from the receiving end of the tubular barrel to prevent the dispersion funnel assembly from being moved toward the dispensing end of the tubular barrel until the dispersion funnel assembly is in the closed configuration.

Example 8 is the device of any of Examples 1-7, further including a vial engagement assembly connected to the tubular barrel at the receiving end, the vial engagement assembly configured to selectively engage a plurality of threads along a portion of a length of the vial.

Example 9 is a system for aseptic storage and delivery of biological material. The system includes a vial and a delivery device. The vial includes a tubular body to contain the biological material until delivery, a vial input port, and a pressure activated vial output port. The delivery device is according to any of Examples 1-8.

Example 10 is a method for the aseptic delivery of biological material that is in an aseptically frozen and condensed state within a vial using a delivery device. The method includes thawing the biological material contained within the vial, connecting the vial to the delivery device to transfer the thawed biological material into the delivery device, dispersing the thawed biological material within the delivery device, and forcing the dispersed biological material out of the delivery device and into an intravascular device connected to the delivery device.

Example 11 is the method of Example 10, wherein connecting the vial to the delivery device includes connecting a vial output port to an input port of an inner funnel of a dispersion funnel assembly, inserting the inner funnel into an outer funnel of the dispersion funnel assembly within a tubular barrel of the delivery device, at least one projection on the inner funnel engaging an axially extending slot within the outer funnel to align a first plurality of openings in the inner funnel with a second plurality of openings in the outer funnel, and moving the vial to push the inner funnel through the outer funnel until at least one cantilevered lug on the inner funnel engages at least one first recess in the outer funnel to place the dispersion funnel assembly in an open configuration.

Example 12 is the method of Example 11, wherein dispersing the biological material within the delivery device includes connecting a source of liquid to a vial input port, flowing the liquid into the vial to force the biological material out of the vial, into the inner funnel, through the first plurality of openings, into the outer funnel, through the second plurality of openings, and into the tubular barrel, and flowing the liquid through a filter assembly connected to a dispensing end of the tubular barrel. At least one of the first plurality of openings or the second plurality of openings is sized to permit the liquid and dispersed biological material to pass through the dispersion funnel assembly and prevent undispersed biological material from passing through the dispersion funnel assembly. The filter assembly includes a filter medium. The filter medium is sized to prevent the dispersed biological material from passing through the filter assembly but to permit the liquid to pass through the filter assembly.

Example 13 is the he method of Example 12, wherein forcing the dispersed biological material out of the delivery device and into the intravascular device connected to the delivery device includes moving the vial to push the inner funnel through the outer funnel, disengaging the at least one cantilevered lug from the at least one first recess and then engaging at least one second recess in the outer funnel, forcing a seal between the inner funnel and the outer funnel to close to place the dispersion funnel assembly in a closed configuration to prevent the liquid or the dispersed biological material from passing back into the dispersion funnel assembly, selecting the filter assembly to be in a bypass state so the liquid and the dispersed biological material can bypass the filter medium, disengaging a dispersion funnel retaining device configured to prevent the outer funnel from sliding along the tubular barrel by engaging a portion of the outer funnel extending from a receiving end of the tubular barrel, and moving the vial to force the connected dispersion funnel assembly to slide along the tubular barrel and toward the dispensing end of the tubular barrel, the dispersion funnel assembly forcing the biological material through the filter assembly and into the intravascular device connected to the delivery device.

Example 14 is the method of Example 13, further including removing a retaining sleeve disposed around a portion of the vial before moving the vial, the retaining sleeve configured to prevent moving the vial to push the inner funnel through the outer funnel to disengage the at least one cantilevered lug from the at least one first recess.

Example 15 is the method of any of Examples 11-14, wherein, the connection between the vial and the dispersion funnel assembly is a rotatable connection and moving the vial includes engaging a threaded portion the tubular body with a vial engagement assembly connected to the tubular barrel and rotating the vial to thread the vial through the vial engagement assembly and move the vial relative to the delivery device.

Example 16 is a device for aseptic delivery of biological material from a vial. The device includes a tubular barrel, a filter assembly, and a dispersion funnel assembly. The tubular barrel includes a receiving end to accept a portion of the vial within the tubular barrel and a dispensing end opposite the receiving end. The filter assembly is fluidly connected to the dispensing end of the tubular barrel. The dispersion funnel assembly is configured to connect to the vial and to be at least partially disposed within the tubular barrel. The dispersion funnel assembly has an open configuration to disperse the biological material from the vial into the tubular barrel between the dispersion funnel assembly and the filter assembly, and a closed configuration to force the dispersed biological material through the filter assembly when the dispersion funnel assembly is moved toward the dispensing end of the tubular barrel.

Example 17 is the device of Example 16, wherein the filter assembly includes a filter medium, the filter assembly selectable between an open state wherein the filter medium prevents the biological material from passing through the filter assembly but permits liquid to pass through the filter assembly, a bypass state wherein the biological material can pass through the filter assembly to deliver the biological material, and, optionally, a closed state wherein no liquid or biological material can pass through the filter assembly.

Example 18 is the device of Example 17, wherein the filter assembly is only selectable from the closed state to the open state and from the open state to the bypass state.

Example 19 is the device of Example 17, wherein the filter assembly further includes a first output port and as second output port. The first output port is in fluid communication with the dispensing end of the tubular barrel when the filter assembly is in the open state. The second output port is in fluid communication with the dispensing end of the tubular barrel when the filter assembly is in the bypass state.

Example 20 is the device of any of Examples 16-19, wherein the dispersion funnel assembly includes an inner funnel, and outer funnel, and a compressible seal. The inner funnel includes a first plurality of openings through the inner funnel. The outer funnel includes a second plurality of openings through the outer funnel. The inner funnel is coaxial with and nested within the outer funnel such that the first plurality of openings are aligned with the second plurality of openings. The compressible seal is disposed between the inner funnel and the outer funnel. In the open configuration, the compressible seal permits a fluid connection between the inner funnel and the outer funnel. In the closed configuration, the compressible seal is compressed between the inner funnel and the outer funnel to prevent the fluid connection between the inner funnel and the outer funnel.

Example 21 is the device of Example 20, wherein the inner funnel further includes a first tubular portion and a first conical portion coaxial with and projecting away from the first tubular portion and the outer funnel further includes a second tubular portion and a second conical portion coaxial with and projecting away from the second tubular portion. The first conical portion defines a first opening angle and the first plurality of openings. The second conical portion defines a second opening angle and the second plurality of openings. The second opening angle is substantially equal to the first opening angle.

Example 22 is the device of either of Examples 20 or 21, further including a dispersion funnel retaining device configured to engage a portion of the outer funnel extending from the receiving end of the tubular barrel to prevent the dispersion funnel assembly from being moved toward the dispensing end of the tubular barrel until the dispersion funnel assembly is in the closed configuration.

Example 23 is the device of any of Examples 16-22, further including a vial engagement assembly connected to the tubular barrel at the receiving end. The vial engagement assembly is configured to selectively engage a plurality of threads along a portion of a length of the vial.

Example 24 is a system for aseptic storage and delivery of biological material. The system includes a vial and a delivery device. The vial includes a tubular body to contain the biological material until delivery, a vial input port, and a pressure activated vial output port. The delivery device is configured to connect to the vial to deliver the biological material. The delivery device includes a tubular barrel, a filter assembly, and a dispersion funnel assembly. The tubular barrel includes a receiving end to accept at least a portion of the vial including the output port within the tubular barrel, and a dispensing end opposite the receiving end. The filter assembly is fluidly connected to the dispensing end of the tubular barrel. The dispersion funnel assembly is configured to connect to the vial output port. The dispersion funnel assembly is configured to be at least partially disposed within the tubular barrel. The dispersion funnel assembly has an open configuration to disperse the biological material from the vial into the tubular barrel between the dispersion funnel assembly and the filter assembly, and a closed configuration to force the dispersed biological material through the filter assembly when the dispersion funnel assembly is moved toward the dispensing end of the tubular barrel.

Example 25 is the system of Example 24, wherein the filter assembly includes a filter medium. The filter assembly is selectable between an open state wherein the filter medium prevents the biological material from passing through the filter assembly but permits liquid to pass through the filter assembly, a bypass state wherein the biological material can pass through the filter assembly to deliver the biological material, and optionally, a closed state wherein no liquid or biological material can pass through the filter assembly.

Example 26 is the system of either of Examples 24 or 25, wherein the dispersion funnel assembly includes an inner funnel, an outer funnel, and a compressible seal. The inner funnel includes a first plurality of openings through the inner funnel. The outer funnel includes a second plurality of openings through the outer funnel. The inner funnel is coaxial with and nested within the outer funnel such that the first plurality of openings are aligned with the second plurality of openings. The compressible seal is disposed between the inner funnel and the outer funnel. In the open configuration, the compressible seal permits a fluid connection between the inner funnel and the outer funnel. In the closed configuration, the compressible seal is compressed between the inner funnel and the outer funnel to prevent the fluid connection between the inner funnel and the outer funnel.

Example 27 is the system of Example 26, wherein the inner funnel further includes a first tubular portion and a first conical portion coaxial with and projecting away from the first tubular portion. The outer funnel further includes a second tubular portion and a second conical portion coaxial with and projecting away from the second tubular portion. The first conical portion defines a first opening angle and the first plurality of openings. The second conical portion defines a second opening angle and the second plurality of openings. The second opening angle is substantially equal to the first opening angle.

Example 28 is the system of either of Examples 26 or 27, wherein the delivery device further includes a dispersion funnel retaining device configured to engage a portion of the outer funnel extending from the receiving end of the tubular barrel to prevent the dispersion funnel assembly from being moved toward the dispensing end of the tubular barrel until the dispersion funnel assembly is in the closed configuration.

Example 29 is the system of any of Examples 24-28, wherein a portion of a length of the tubular body of the vial includes a plurality of threads, and the delivery device further includes a vial engagement assembly connected to the tubular barrel at the receiving end, the vial engagement assembly configured to selectively engage the plurality of threads.

Example 30 is a method for the aseptic delivery of biological material that is in an aseptically frozen and condensed state within a vial using a delivery device. The method includes thawing the biological material contained within the vial, connecting the vial to the delivery device to transfer the thawed biological material into the delivery device, dispersing the thawed biological material within the delivery device, and forcing the dispersed biological material out of the delivery device and into an intravascular device connected to the delivery device.

Example 31 is the method of Example 30, wherein connecting the vial to the delivery device includes connecting a vial output port to an input port of an inner funnel of a dispersion funnel assembly, inserting the inner funnel into an outer funnel of the dispersion funnel assembly within a tubular barrel of the delivery device, at least one projection on the inner funnel engaging an axially extending slot within the outer funnel to align a first plurality of openings in the inner funnel with a second plurality of openings in the outer funnel, and moving the vial to push the inner funnel through the outer funnel until at least one cantilevered lug on the inner funnel engages at least one first recess in the outer funnel to place the dispersion funnel assembly in an open configuration.

Example 32 is the method of Example 31, wherein dispersing the biological material within the delivery device includes connecting a source of liquid to a vial input port, flowing the liquid into the vial to force the biological material out of the vial, into the inner funnel, through the first plurality of openings, into the outer funnel, through the second plurality of openings, and into the tubular barrel, and flowing the liquid through a filter assembly connected to a dispensing end of the tubular barrel. The filter assembly includes a filter medium. The filter medium is sized to prevent the dispersed biological material from passing through the filter assembly but to permit the liquid to pass through the filter assembly. At least one of the first plurality of openings or the second plurality of openings is sized to permit the liquid and dispersed biological material to pass through the dispersion funnel assembly and prevent undispersed biological material from passing through the dispersion funnel assembly.

Example 33 is the method of Example 32, wherein forcing the dispersed biological material out of the delivery device and into the intravascular device connected to the delivery device includes moving the vial to push the inner funnel through the outer funnel, disengaging the at least one cantilevered lug from the at least one first recess and then engaging at least one second recess in the outer funnel, forcing a seal between the inner funnel and the outer funnel to close to place the dispersion funnel assembly in a closed configuration to prevent the liquid or the dispersed biological material from passing back into the dispersion funnel assembly, selecting the filter assembly to be in a bypass state so the liquid and the dispersed biological material can bypass the filter medium, disengaging a dispersion funnel retaining device configured to prevent the outer funnel from sliding along the tubular barrel by engaging a portion of the outer funnel extending from a receiving end of the tubular barrel, and moving the vial to force the connected dispersion funnel assembly to slide along the tubular barrel and toward the dispensing end of the tubular barrel, the dispersion funnel assembly forcing the biological material through the filter assembly and into the intravascular device connected to the delivery device.

Example 34 is the method of Example 33, further including removing a retaining sleeve disposed around a portion of the vial before moving the vial, the retaining sleeve configured to prevent moving the vial to push the inner funnel through the outer funnel to disengage the at least one cantilevered lug from the at least one first recess.

Example 35 is the method of any of Examples 31-34, wherein, the connection between the vial and the dispersion funnel assembly is a rotatable connection and moving the vial includes engaging a threaded portion the tubular body with a vial engagement assembly connected to the tubular barrel and rotating the vial to thread the vial through the vial engagement assembly and move the vial relative to the delivery device.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
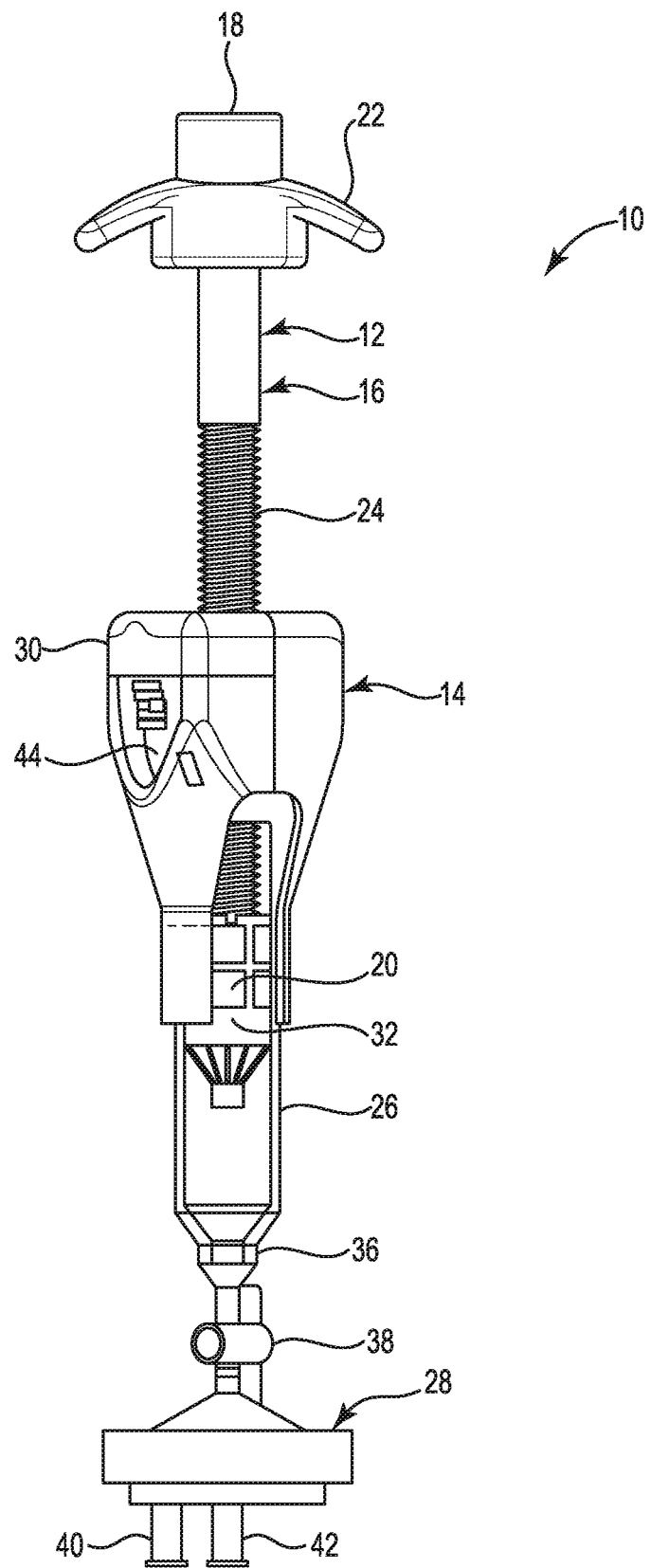
FIG. 1 is a perspective view of a system for aseptic storage and delivery of biological material, according to some embodiments of the disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Embodiments of the present disclosure include a system for the aseptic storage and delivery of biological material, such as transplant cells for cellular therapy. Embodiments can provides for a closed aseptic system beginning after the production of the transplant cells and maintains the closed aseptic system for the transplant cells through freezing, transport, storage, thawing, washing, and delivery into the patient.

FIG. 1 is a perspective view of a system 10 for aseptic storage and delivery of biological material, according to embodiments of the disclosure. As shown in FIG. 1, the system 10 includes a vial 12 and a delivery device 14. The vial 12 can include a tubular body 16, a vial input port 18, a vial output port 20, a handle 22 and a plurality of threads 24. In the embodiment of FIG. 1, the vial input port 18 and the vial output port 20 are located at opposite ends of the tubular body 16. The handle 22 can be located near the vial input port 18. The plurality of threads 24 can extend along at least a portion of the tubular body 16.

Figure 11A:
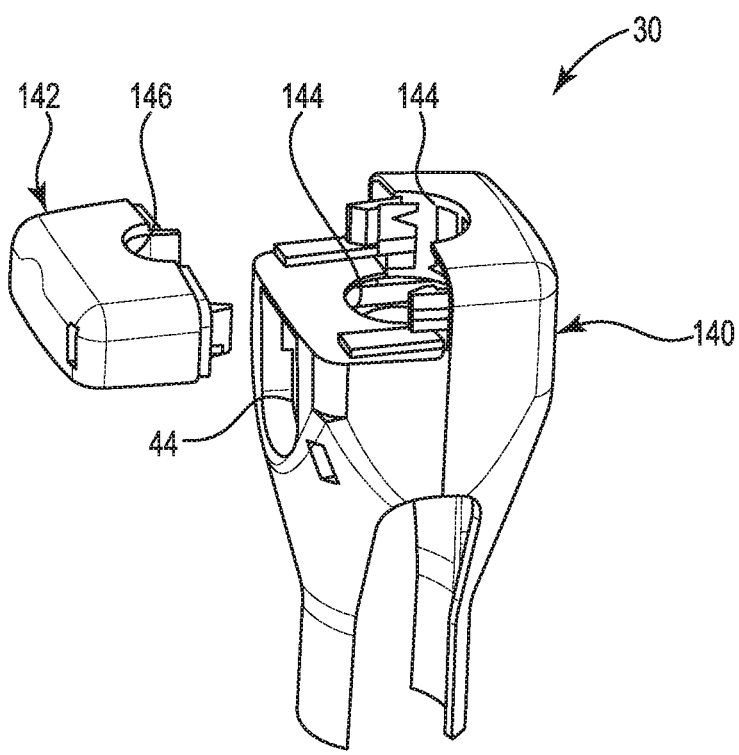
FIGS. 11A-11C are views of a vial engagement assembly of the delivery device of FIG. 1, according to some embodiments.
Figure 11B:
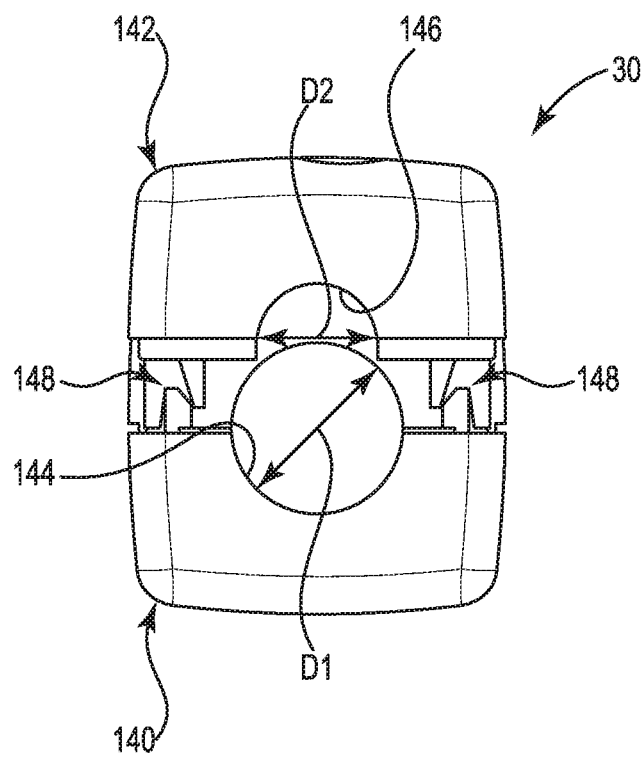
Figure 11C:
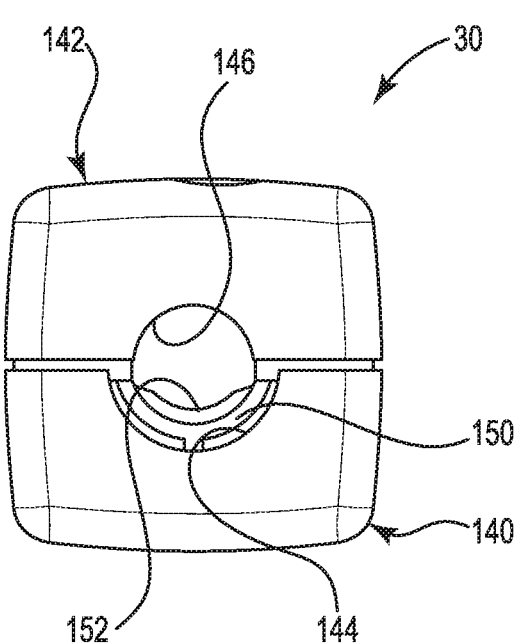

The delivery device 14 can include a tubular barrel 26 (shown as transparent), a filter assembly 28, a vial engagement assembly 30, and a dispersion funnel assembly 32. The tubular barrel 26 includes a receiving end 34 (not visible within the vial engagement assembly 30, see FIG. 7) and a dispensing end 36 opposite the receiving end 34. The filter assembly 28 can include a stopcock 38, a filter output port 40 and a bypass output port 42. The vial engagement assembly 30 can include a thread disengagement pushbutton 44 for selectively disengaging the plurality of threads 24, as described below in reference to FIGS. 11A-11C.

The filter assembly 28 is fluidly connected to the dispensing end 36 of the tubular barrel 26. The vial engagement assembly 30 is connected to the receiving end 34 (FIG. 7) of the tubular barrel 26. The dispersion funnel assembly 32 is configured to connect to the vial output port 20, as described in further detail below in reference to FIG. 6. The dispersion funnel assembly 32 is disposed at least partially within the tubular barrel 26 and can be slideably engaged with the tubular barrel 26. So configured, the vial 12, the connected dispersion funnel assembly 32, and the tubular barrel 26 can act as a syringe, with the vial 12 and the connected dispersion funnel assembly 32 acting together as a plunger and the tubular barrel 26 acting as the syringe body.

The dispersion funnel assembly 32 has an open configuration and a closed configuration, as described in detail below in reference to FIGS. 5A and 5B. In the open configuration, biological material within the vial 12 can be forced out of the vial 12 by a flow of liquid (such as a saline solution or a delivery matrix) connected to the vial input port 18 and into the dispersion funnel assembly 32, and be dispersed from the dispersion funnel assembly 32 into the tubular barrel 26 between the dispersion funnel assembly 32 and the filter assembly 28 (described in further detail below in reference to FIG. 13). The filter assembly 28 can be configured to be in an open state in which a filter medium 134 (shown in FIG. 10) prevents the dispersed biological material from passing through the filter assembly 28 but permits the liquid to pass through the filter assembly 28 and out through the filter output port 40 to permit the flow of liquid through the vial 12 and the delivery device 14.

In the closed configuration, the dispersion funnel assembly 32 prevents the dispersed biological material from passing back into the dispersion funnel assembly 32 when the attached the vial 12 is moved to slide the dispersion funnel assembly 32 toward the filter assembly 28. Thus, when the dispersion funnel assembly 32 is in the closed configuration, the vial 12 and dispersion funnel assembly 32 can act as the plunger. In some embodiments, once the biological material has been dispersed into the tubular barrel 26, a source of liquid (such as a saline solution or a delivery matrix) can be connected to the filter output port 40, and the vial 12 and dispersion funnel assembly 32 can be pulled away from the filter assembly 28, drawing liquid across the filter medium 134 to dislodge dispersed biological material from the filter medium 134, and to provide a desired concentration of biological material and liquid for delivery to the patient.

Once the dispersed biological material and liquid are ready for delivery to the patient, the stopcock 38 can be closed, and the filter assembly 28 can be configured to be in a bypass state in which the dispersed biological material and liquid can pass through the filter assembly 28 and out through the bypass output port 42 to the patient by way of an intravascular device (not shown) attached to the bypass output port 42. Such intravascular devices can include, for example, intravenous lines or needles. Once the filter assembly 28 is configured to be in the bypass state and the intravascular device is attached to the bypass output port 42, the stopcock 38 can be opened, and the vial 12 moved toward the dispensing end 36 of the tubular barrel 26 to force the dispersion funnel assembly 32 toward the filter assembly 28 to deliver the biological material and liquid to the patient.

In the embodiment shown in FIG. 1, the vial 12 can be moved relative to the delivery device 14 in a precise fashion by rotating the vial 12 to screw the vial 12 into or out of the delivery device 14 as the plurality of threads 24 threadily engage the vial engagement assembly 30. The handle 22 may be grasped to ease rotation of the vial 12. Should less precise and/or faster control of the movement of vial 12 relative to the delivery device 14 is desired, the thread disengagement pushbutton 44 can be pressed (as shown in FIG. 1) to disengage the vial engagement assembly 30 from the plurality of threads 24, permitting the vial 12 to be moved relative to the delivery device 14 by pushing or pulling on the vial 12, as one would with a syringe, without requiring rotation of the vial 12.

Figure 2:
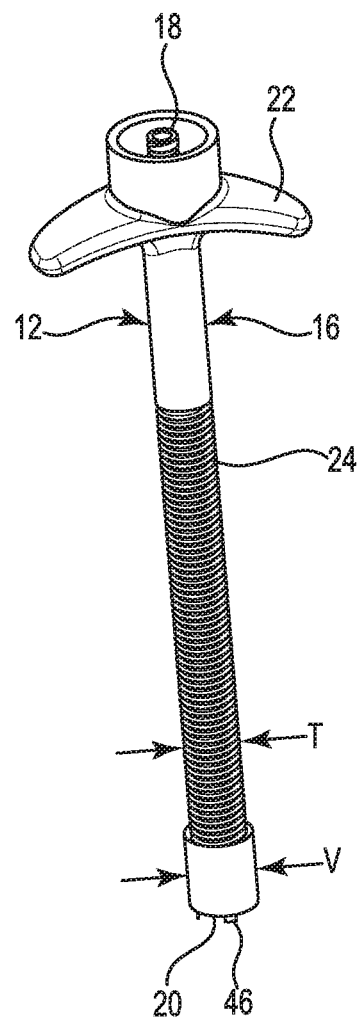
FIG. 2 is a perspective view of a vial of FIG. 1, according to some embodiments.
Figure 3:
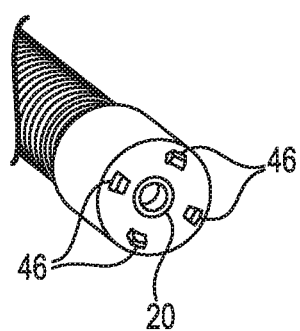
FIG. 3 is an enlarged perspective view of a portion of the vial of FIG. 2, according to some embodiments.

FIG. 2 is a perspective view of the vial 12 of FIG. 1, according to some embodiments. FIG. 3 is an enlarged perspective view of a portion of the vial 12 of FIG. 2 including the vial output port 20, according to some embodiments. As shown in FIG. 2, and more clearly in FIG. 3, the vial 12 can further include a plurality of flexible, cantilevered lugs 46 arranged about the vial output port 20. The plurality of cantilevered lugs 46 can be employed to connect the dispersion funnel assembly 32 to the vial output port 20, as described in further detail below in reference to FIG. 6. Although four cantilevered lugs 46 are shown in the embodiment of FIG. 3, it is understood that embodiments can include any number of cantilevered lugs 46 greater than or equal to two. In other embodiments, a single continuous annular cantilevered lug 46 encircling the vial output port 20 may be employed. In some embodiments, the plurality of threads 24 have a thread diameter T and a portion of the vial 12 including the vial output port 20 and the cantilevered lugs 46 has a diameter V that is greater than the thread diameter T.

The vial 12 is a tubular container that can be formed of any material that remains structurally sound after lengthy exposure to cryogenic temperatures and is suitable for use with biological materials. That is, the material does not present a source of contamination to the biological, for example, from materials leaching out of the material. Suitable materials can include polymer materials, such as polypropylene, polyamide, or polyimide. The vial input port 18 and vial output port 20 can be any type of connectors for use with intravenous lines. For example, in the embodiment shown in FIGS. 2 and 3, the vial input port 18 is a female luer connector and the vial output port 20 is a male luer connector. In some embodiments, the vial output port 20 is a pressure activated output port. That is, liquid will not flow out of the vial output port 20 until sufficient hydraulic pressure is applied across the vial output port 20, as discussed in further detail below in reference to FIGS. 12 and 13. In some embodiments, the vial input port 18 and the vial output port 20 each include a double sterile seal (not shown). The biological material can be loaded into the vial 12 and then the two sets of double sterile seals can be applied.

In some embodiments, after the biological material is washed and suspended in a solution including proteins and a cryoprotectant, such as dimethylsulfoxide (DMSO), the biological material can be centrifuged and the supernatant aspirated off to produce a condensed clump of cells in a "pellet" form. The biological material in the vial 12 can be frozen in this condensed form to provide for a large number of cells in a relatively compact storage form factor. Thus, the vial 12 can be much smaller than the bag typically employed for the transportation and storage of biological material, as discussed above. The smaller form factor of the vial 12 is easier to transport and requires less freezer space, which can reduce costs. The vial 12 can be a compact and efficient device for the transportation and storage of the biological material.

Figure 4:
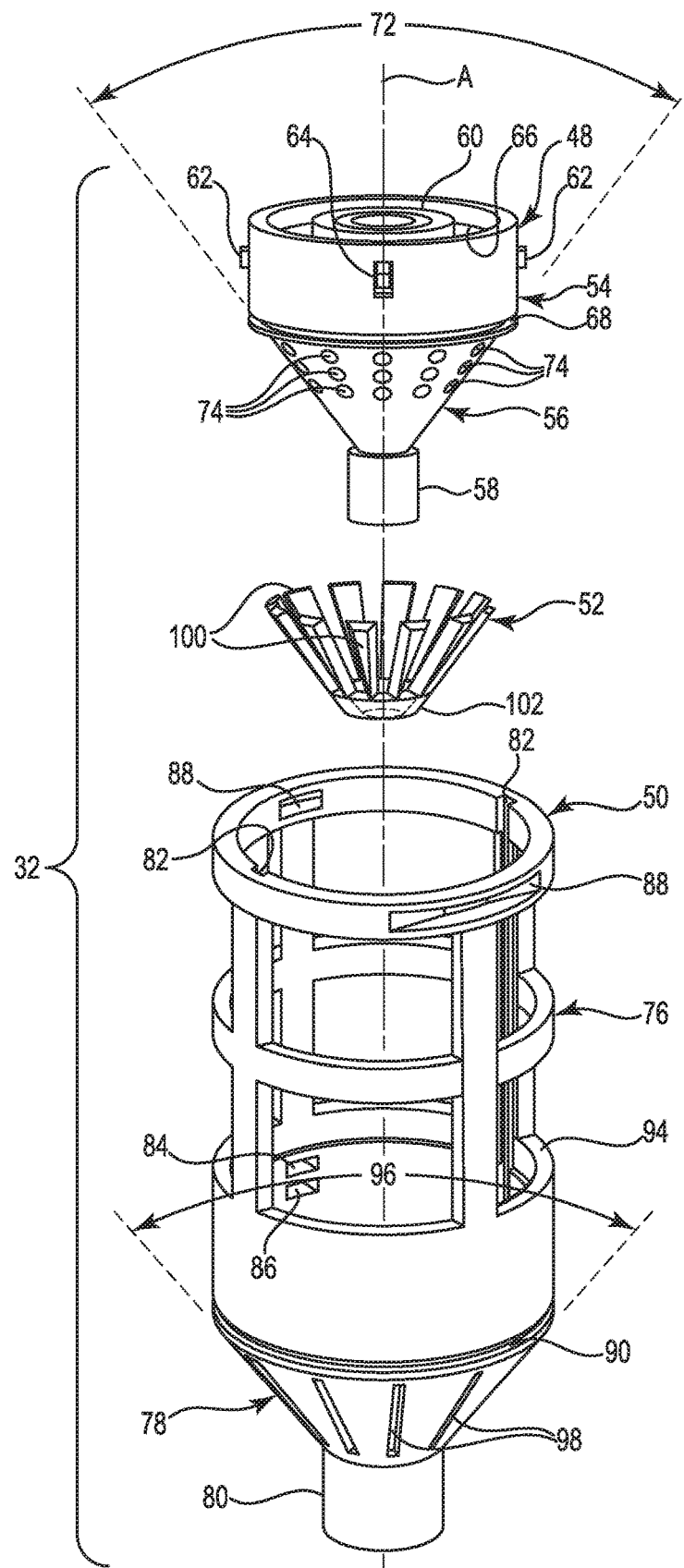
FIG. 4 is an exploded perspective view of a dispersion funnel assembly of a delivery device of FIG. 1, according to some embodiments.

FIG. 4 is an exploded perspective view of the dispersion funnel assembly 32 of the delivery device 14 of FIG. 1, according to some embodiments. As shown in FIG. 4, the dispersion funnel assembly 32 includes an inner funnel 48, an outer funnel 50, and a compressible seal 52. The inner funnel 48 is a closed funnel (shown in FIG. 12) that includes a first tubular portion 54, a first conical portion 56, and a first base portion 58. The first tubular portion 54 includes a funnel input port 60, at least one projection 62 (two shown), a least one flexible, cantilevered lug 64 (one shown, one on the opposite side), a circular recess 66, and a first O-ring channel 68. The funnel input port 60 faces axially along an axis A of the dispersion funnel assembly 32. The funnel input port 60 can be any type of connector for use with the vial output port 20. In this way, the dispersion funnel assembly 32 is configured to connect to the vial output port 20. For example, in the embodiment shown in FIG. 4, the funnel input port 60 is a female luer connector. The at least one projection 62 projects radially outward from the first tubular portion 54. A lug portion of the at least one cantilevered lug 64 projects radially from the first tubular portion 54. The circular recess 66 is formed around the inside of the first tubular portion 54. The first O-ring channel 68 is formed around the outside of the first tubular portion 54 for containing a first O-ring 70 (shown in FIG. 6). The first conical portion 56 defines a first opening angle 72 and a first plurality of openings 74 through the first conical portion 56. The first conical portion 56 is coaxial with the axis A and projects away from the first tubular portion 54, tapering from the first tubular portion 54 to the first base portion 58. The first conical portion 56 is recessed radially inward from the first tubular portion 54 to the first base portion 58 to accommodate the compressible seal 52.

The outer funnel 50 is an open funnel that includes a second tubular portion 76, a second conical portion 78, and a second base portion 80. The second tubular portion 76 includes, at least one slot 82 (two shown), at least one first recess 84 (one shown and one on the opposite side), at least one second recess 86 (one shown and one on the opposite side), at least one dispersion funnel retaining slot 88 (two shown), and a second O-ring channel 90. The second tubular portion 76 may also include a plurality of cutouts 94 as shown in FIG. 4. The at least one slot 82 is formed on the inside of the second tubular portion 76 and extends axially from an end of the second tubular portion 76 opposite the second conical portion 78 toward the second conical portion 78. The at least one slot 82 is sized to accommodate the at least one projection 62 of the inner funnel 48 in a sliding arrangement, with a slot 82 for each projection 62. The at least one first recess 84 is formed on the inside of the second tubular portion 76. The at least one second recess 86 is also formed on the inside of the second tubular portion 76. The at least one second recess 86 is circumferentially aligned with, and spaced axially apart from, the at least one first recess 84. The at least one first recess 84 and the at least one second recess 86 are sized to accommodate the at least one cantilevered lug 64 of the inner funnel 48, with a first recess 84 and second recess 86 for each cantilevered lug 64. The at least one dispersion funnel retaining slot 88 extends tangentially through the outside of the second tubular portion 76. In some embodiments, the at least one dispersion funnel retaining slot 88 extends in a plane perpendicular to the axis A. The second O-ring channel 90 is formed around the outside of the second tubular portion 76 for containing a second O-ring 92 (shown in FIG. 6). The second O-ring 92 permits the dispersion funnel assembly 32 to be slideably engaged within the tubular barrel 26 and to provide a seal between the dispersion funnel assembly 32 and the tubular barrel 26.

Figure 12:
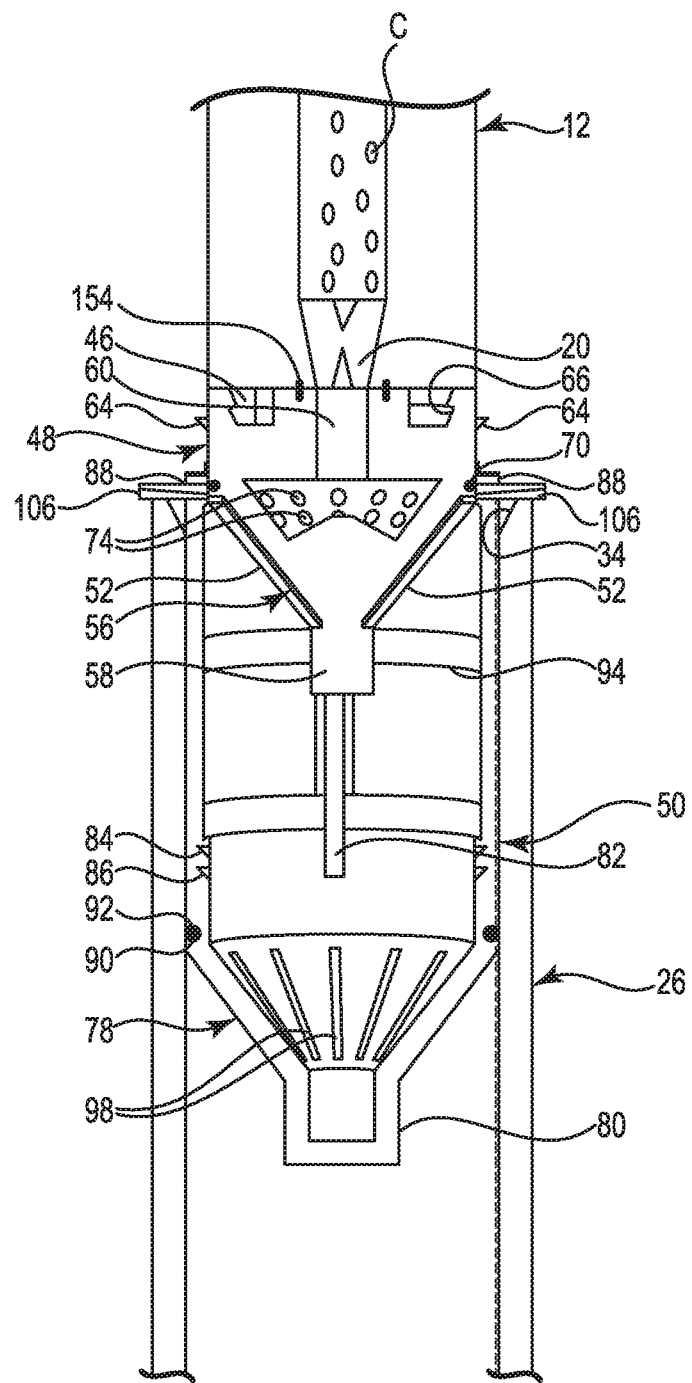
FIG. 12 is a schematic cross-sectional view further illustrating the system of FIG. 1 and a method for aseptic storage and delivery of biological material, according to embodiments of the disclosure.

The plurality of cutouts 94 may be formed to reduce the surface area in contact with the first O-ring 70 when the inner funnel 48 is inserted into the outer funnel 50 (FIG. 12). The second conical portion 78 defines a second opening angle 96 and a second plurality of openings 98 through the second conical portion 78. The second conical portion 78 is coaxial with the axis A and projects away from the second tubular portion 76, tapering from the second tubular portion 76 to the second base portion 80.

In the embodiment shown in FIG. 4, the compressible seal 52 includes a plurality of compressible linear seals 100 projecting from a seal base 102. The seal base 102 is a ring that is expandable to fit around the first base portion 58 of the inner funnel 48 so that the compressible seal 52 can be moved onto the first conical portion 56 which is recessed radially inward from the first tubular portion 54 to the first base portion 58 to accommodate the compressible seal 52. The compressible seal 52 can be formed of any compressible, biocompatible polymer, for example, silicone or polytetrafluoroethylene.

The inner funnel 48 can be nested within the outer funnel 50 such that it is coaxial with the outer funnel 50. The compressible seal 52 can be disposed between the inner funnel 48 and the outer funnel 50, such that it is adjacent to the first conical portion 56 and the second conical portion 78. In some embodiments, the second opening angle 96 is substantially equal to the first opening angle 72 to help provide a consistent seal between the inner funnel 48 and the outer funnel 50.

In the embodiment shown in FIG. 4, each of the first plurality of openings 74 is a hole in a row of holes extending along a portion of a line extending form an apex to a base of the first conical portion 56. The holes are sized such that they will disperse the cells by permitting the passage of transplant cells, but not permitting the passage of clumps of transplant cells. In some embodiments the holes can be as small as 0.1 millimeters (mm). In the embodiment shown in FIG. 4, each of the second plurality of openings 98 is a slit extending radially along a portion of a line extending from an apex to a base of the second conical portion 78. Each of the second plurality of openings 98 is large enough that it will not interfere with the flow of material through the first plurality of openings 74 in the open configuration.

In other embodiments, the first plurality of openings 74 can be slits as described above, and the second plurality of openings 98 can be holes, as described above. In still other embodiments, the first plurality of openings 74 and the second plurality of openings 98 can all be holes as described above. Many opening shapes and combinations are possible, so long as at least one of the first plurality of openings 74 and the second plurality of openings 98 are sized such that they will disperse the cells by permitting the passage of transplant cells, but not permitting the passage of clumps of transplant cells.

Figure 5A:
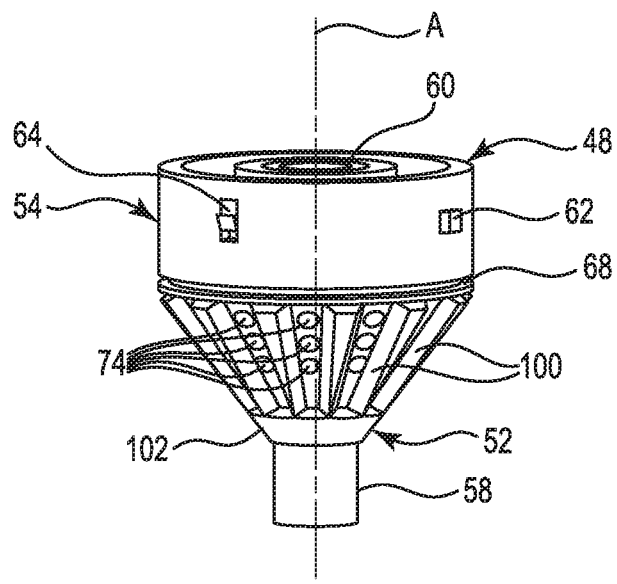
FIGS. 5A and 5B are perspective views of a portion of the dispersion funnel assembly of FIG. 4 in an open configuration and in a closed configuration, respectively, according to some embodiments.
Figure 5B:
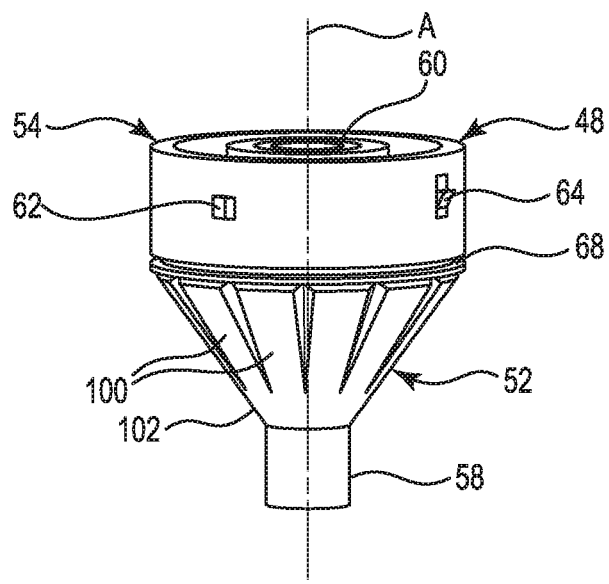

FIGS. 5A and 5B are perspective views of the dispersion funnel assembly 32 of FIG. 4 in the open configuration and in the closed configuration, respectively, according to some embodiments. The compressible seal 52 is moved onto the first conical portion 56. The outer funnel 50 is omitted for clarity. As shown in FIG. 5A, the compressible linear seals 100 are disposed between the rows of the first plurality of openings 74 and aligned so that when the compressible linear seals 100 are largely or completely uncompressed, the compressible linear seals 100 do not block any of the first plurality of openings 74 in the open configuration. As shown in FIG. 5B, once the compressible linear seals 100 are compressed between the inner funnel 48 and the outer funnel 50 by moving the inner funnel 48 toward the outer funnel 50 (see FIGS. 13 and 15), the compressible linear seals 100 expand in a circumferential direction to block the first plurality of openings 74 in the closed configuration.

Figure 6:
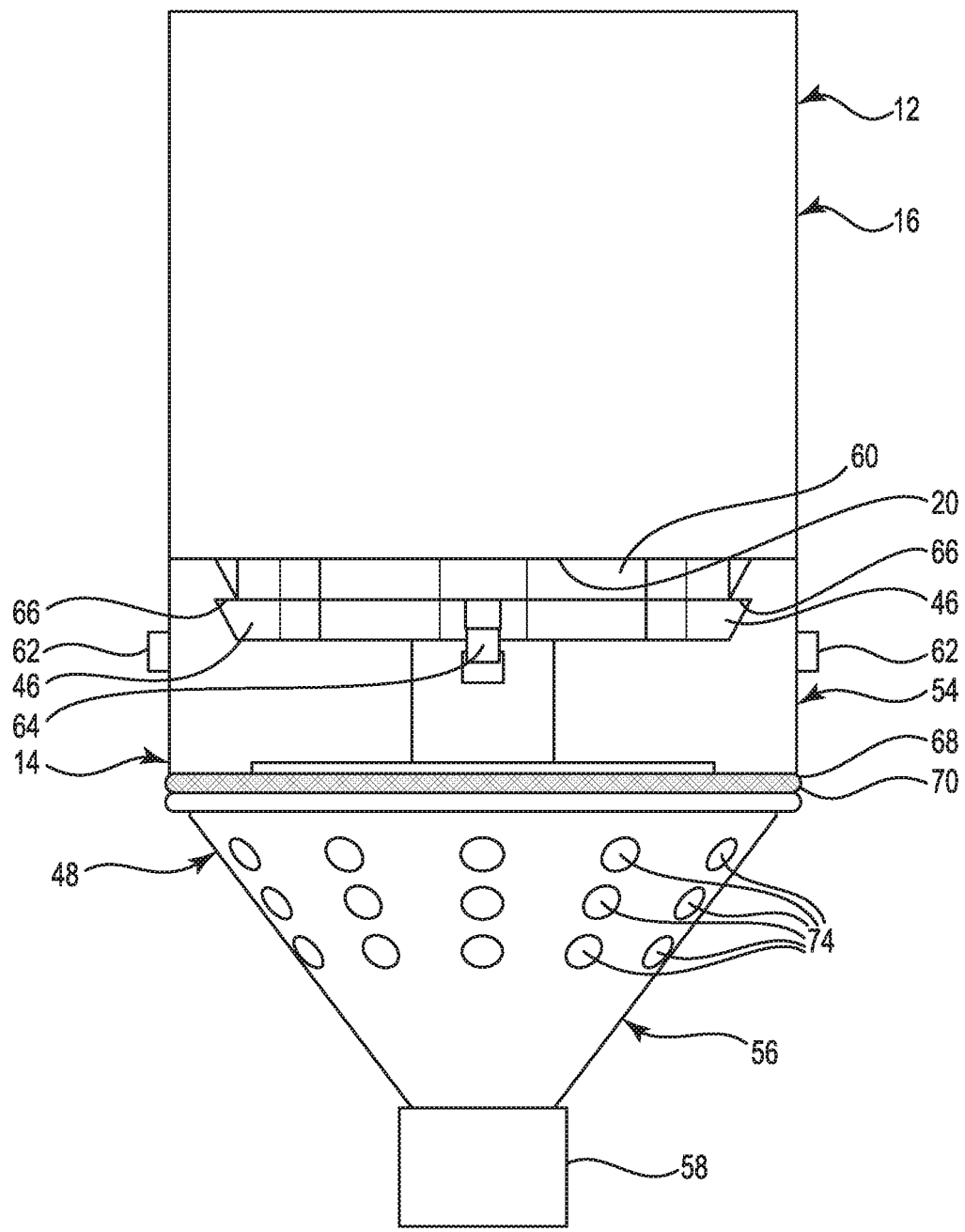
FIG. 6 is a side view of a portion of the system of FIG. 1 showing an interface between the vial and the delivery device, according to some embodiments.

FIG. 6 is a side view of a portion of the system 10 of FIG. 1 showing an interface between the vial 12 and the delivery device 14, according to some embodiments. FIG. 6 shows the vial 12 connected to the inner funnel 48 of the dispersion funnel assembly 32. The first tubular portion 54 is shown as transparent for clarity. The compressible seal 52 is omitted from the figure as it can be moved onto the first conical portion 56 either before the vial 12 is connected to the inner funnel 48 or after (as shown). The first O-ring 70 is shown in the first O-ring channel 68, but it too can be added before or after the vial 12 is connected to the inner funnel 48. As shown in FIG. 6, the vial output port 20 is connected to the funnel input port 60. The plurality of cantilevered lugs 46 can snap into the circular recess 66 formed around the inside of the first tubular portion 54 to form a snap joint. The vial 12 can rotate axially relative to the inner funnel 48 while maintaining the connection between the vial 12 and the dispersion funnel assembly 32 because the circular recess 66 extends uninterrupted around the entire circumference of the inside of the first tubular portion 54.

Figure 7:
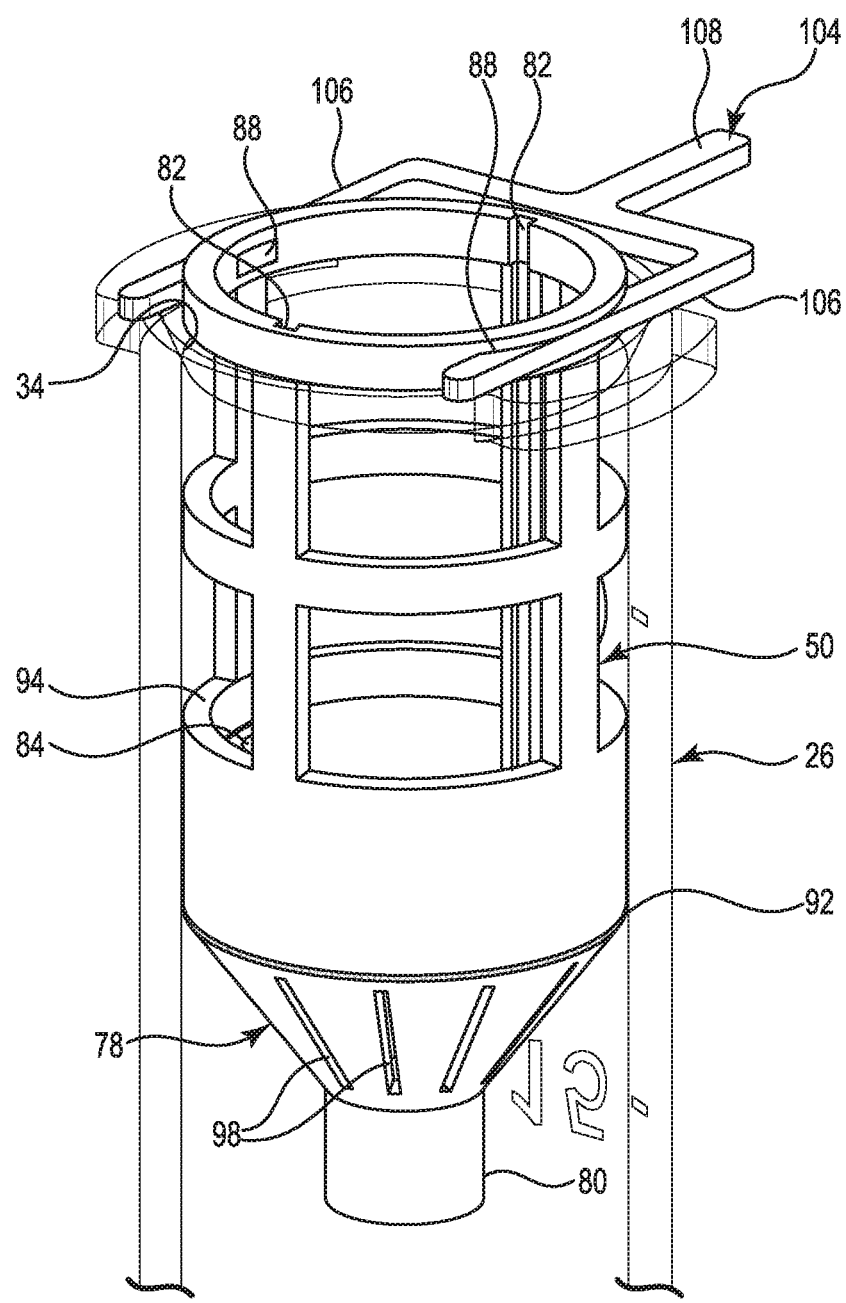
FIG. 7 is a perspective view of a portion of the system of FIG. 1 showing a dispersion funnel retaining device, according to some embodiments.

FIG. 7 is a perspective view of a portion of the system 10 of FIG. 1. FIG. 7 shows the receiving end 34 of the tubular barrel 26 with a portion of the outer funnel 50 projecting from the receiving end 34 so that the at least one dispersion funnel retaining slot 88 is not within the tubular barrel 26. As shown in FIG. 7, the delivery device 14 can further include a dispersion funnel retaining device 104, according to some embodiments. In the embodiment of FIG. 7, the dispersion funnel retaining device 104 includes at least one tine 106 (two shown) connected to a handle 108. The at least one tine 106 is sized such that when the at least one tine 106 engages the at least one dispersion funnel retaining slot 88 of the outer funnel 50, as shown, the outer funnel 50 is prevented from moving further into the tubular barrel 26. Removing the dispersion funnel retaining device 104 by pulling radially on the handle 108 to withdraw the at least one tine 106 completely from the at least one dispersion funnel retaining slot 88 permits the outer funnel 50 to be completely moved into and through the tubular barrel 26. In this way, the dispersion funnel assembly 32 can be prevented from moving toward the dispensing end 36 (FIG. 1) of the tubular barrel 26 until the dispersion funnel assembly 32 is in the closed configuration, as described below in reference to FIGS. 12-15.

Figure 8:
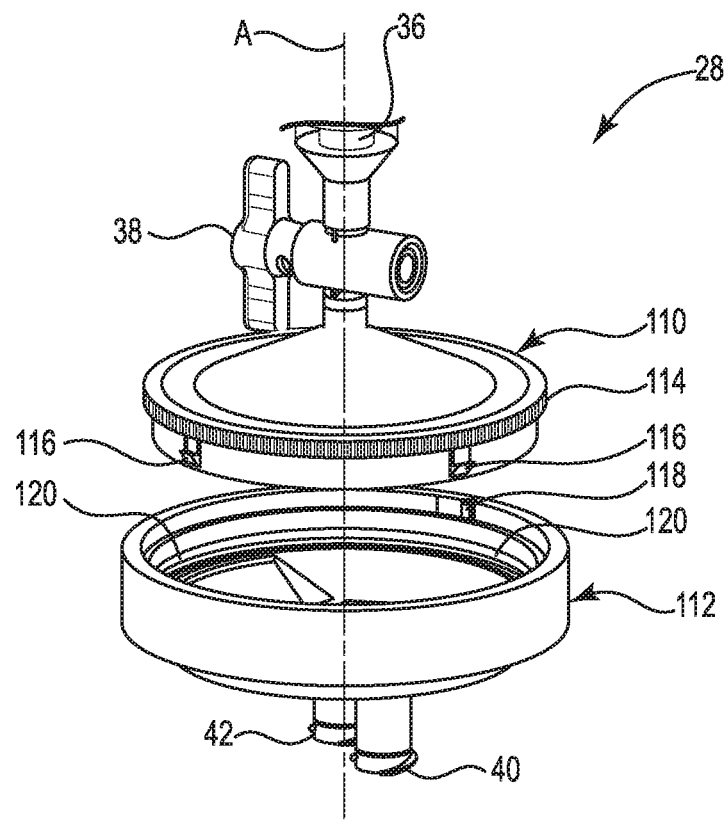
FIG. 8 is an exploded perspective view of a portion of the system of FIG. 1 shown a filter assembly, according to some embodiments.

FIG. 8 is an exploded perspective view of a portion of the system 10 of FIG. 1 shown the filter assembly 28, according to some embodiments. FIG. 8 shows a portion of the tubular barrel 26 including the dispensing end 36 and the filter assembly 28 with the stopcock 38 connected to the dispensing end 36. The tubular barrel 26 is shown as transparent for ease of illustration. As shown in FIG. 8, the filter assembly 28 further includes a round non-rotating member 110 and a round rotating member 112. The non-rotating member 110 includes a plurality of teeth 114 around its circumference and a plurality of cantilevered lugs 116 also around the circumference of the non-rotating member 110, and axially offset from the plurality of teeth 114. The rotating member 112 includes a pawl 118 and a circular recess 120 that extends uninterrupted around the entire circumference of the inside of the rotating member 112.

Figure 9:
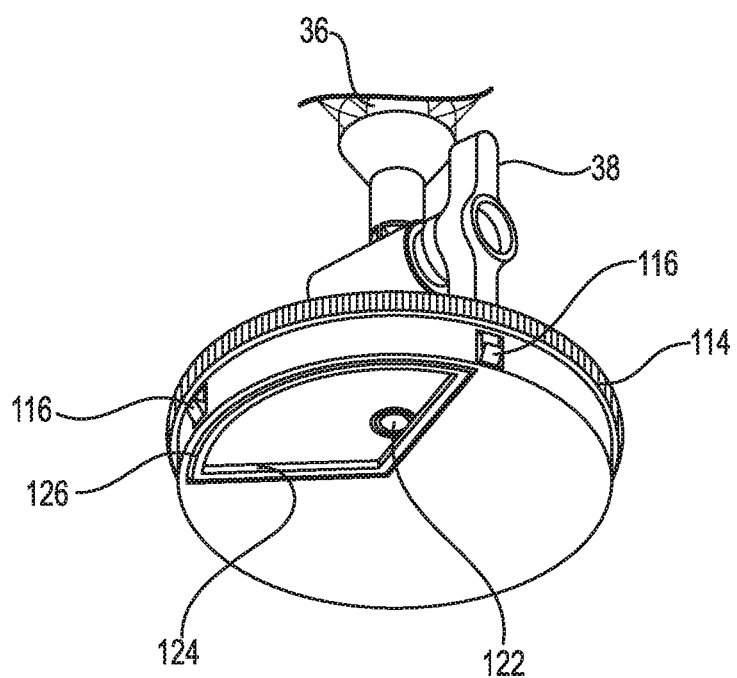
FIG. 9 is a perspective view of a portion of the filter assembly shown in FIG. 8, according to some embodiments.

FIG. 9 is a perspective view of the non-rotating member 110 of the filter assembly 28 shown in FIG. 8, according to some embodiments. As shown in FIG. 9, the non-rotation member 110 further includes a filter inlet 122 connected to the stopcock 38 and opening 124 fluidly connected to the filter inlet 122. The opening 124 is surrounded by an O-ring channel 126.

Figure 10:
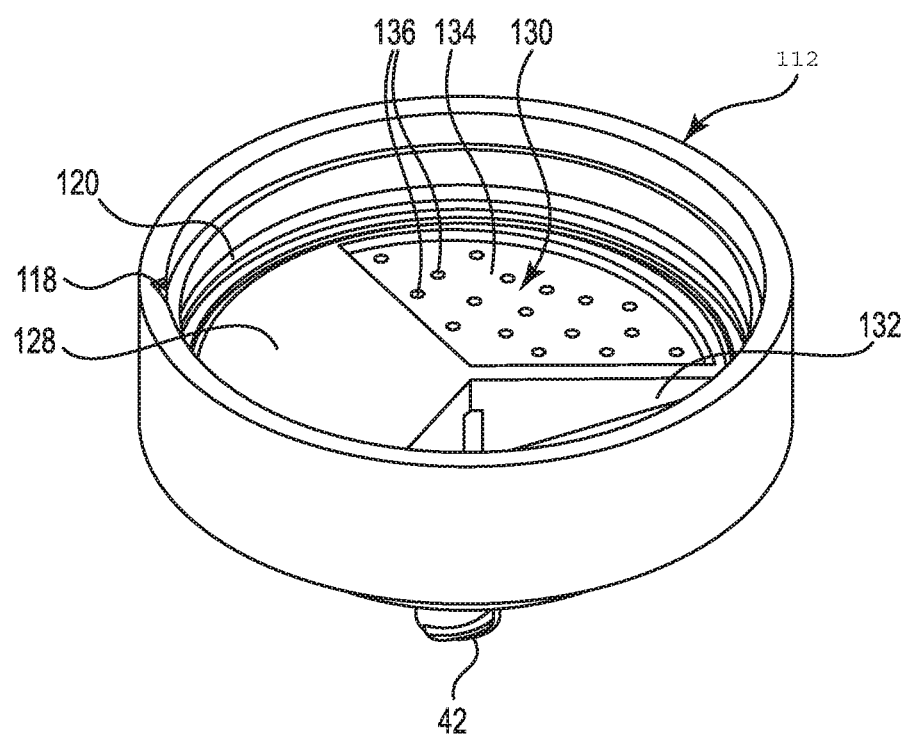
FIG. 10 is a perspective view of another portion of the filter assembly shown in FIG. 8, according to some embodiments.

FIG. 10 is a perspective view of the rotating member 112 of the filter assembly 28 shown in FIG. 8, according to some embodiments. As shown in FIG. 10, the rotating member 112 further includes three filter sections, a closed filter section 128, and open filter section 130, and a bypass filter section 132. The closed filter section 128 is an impermeable barrier that does not permit liquid or biological material to pass. The open filter section 130 includes a filter medium 134. The filter medium 134 is a porous medium including pores 136 that are large enough in diameter to permit the efficient passage of liquids, but small enough to substantially prevent the passage of cells. In some embodiments, the pore size can be as small as, for example, 0.22 microns or 0.45 microns. The filter medium 134 may be made of a material suitable for use with biological materials. That is, the material does not present a source of contamination to the biological, for example, from materials leaching out of the material. Suitable materials include polymer materials, such as polytetrafluoroethylene (PTFE). The bypass filter section 132 can be a largely open section to permit the efficient passage of liquids and biological material.

Considering FIGS. 8-10 together, the filter section 130 is fluidly connected to the filter output port 40 and the bypass section 132 is fluidly connected to the bypass output port 42. The non-rotating member 110 fits into the rotating member 112 such that the cantilevered lugs 116 snap into the circular recess 120 to form a snap joint connecting the rotating member 112 to the non-rotating member 110. The rotating member 112 can rotate axially relative to the non-rotating member 110 while maintaining the connection between the non-rotating member 110 and the rotating member 112 because the circular recess 120 extends uninterrupted around the entire circumference of the inside of the rotating member 112. In other embodiments, a swage joint may be used instead of a snap joint.

The filter assembly 28 is rotatable about the axis A such that any of the three filter sections 128, 130, and 132 can be selected to be in fluid contact with dispensing end 36 of the tubular barrel 26 through the opening 124, the filter inlet 122, and the stopcock 38. The opening 124 and surrounding O-ring channel 126 are sized such that an O-ring (omitted for clarity) in the O-ring channel 126 prevents liquid and biological material flowing out of the opening 124 and into one of the three filter sections 128, 130, and 132 from leaking into either of the other of the three filter sections 128, 130, and 132.

Thus, the filter assembly 28 is selectable between an open state in which the filter medium 134 prevents the biological material from passing through the filter assembly 28 but permits liquid to pass through the filter assembly 28, a bypass state wherein the biological material can pass through the filter assembly 28 to deliver the biological material, and a closed state wherein no liquid or biological material can pass through the filter assembly 28. The open state may be employed during washing of the biological material and dispersal of the cells into the tubular barrel 26. The bypass state may be employed during delivery of the biological material to the patient. The closed state may be employed prior to use of the delivery device 14 to protect the filter medium 134.

The pawl 118 can be angled such that it engages the plurality of teeth 114 to form a one-way ratchet to permit the rotating member 112 to rotate in one direction only. Thus, in this embodiment, the filter assembly 28 is only selectable from the closed state to the open state and from the open state to the bypass state. This arrangement prevents the rotating member 112 from accidentally moved from the closed state directly to the bypass state, which could result in the loss of the biological material. Additionally, or alternatively, the exteriors of the non-rotating member 110 and the rotating member 112 can be marked to provide a visual indicator the state of the filter assembly 28.

In other embodiments, the filter assembly 28 includes only the closed state and the open state. In such embodiments, the rotating member 112 does not include the closed filter section 128 or the pawl 118, and the non-rotating member 110 does not include the plurality of teeth 114.

FIGS. 11A-11C are views of the vial engagement assembly 30 of the delivery device 14 of FIG. 1, according to some embodiments. As discussed above in reference to FIG. 2, in some embodiments, the plurality of threads 24 of the vial 12 have a thread diameter T and the portion of the vial 12 including the vial output port 20 and the cantilevered lugs 46 has a diameter V that is greater than the thread diameter T. The vial engagement assembly 30 is configured to accommodate both diameters of the vial 12. FIG. 11A is an exploded perspective view of the vial engagement assembly 30 showing that the vial engagement assembly 30 includes a main housing 140 and a support housing 142. The main housing 140 devices a first opening 144 through the main housing 140. The support housing 142 includes a second opening 146. The support housing 142 is configured to be selectively connected to the main housing 140.

FIG. 11B is an exploded top view of the vial engagement assembly 30 just as the support housing 142 is being connected to the main housing 140 by two snap joints 148. As shown in FIG. 11B, the first opening 144 has diameter D1 and the second opening 146 has a diameter D2. The diameter D1 is slightly greater than the diameter V of the vial 12 to accommodate passage of the portion of the vial including the vial output port 20 and the cantilevered lugs 46. The diameter D2 is slightly larger than the diameter T, but smaller than either the diameter D1 or the diameter V to provide support for the portion of the vial 12 including the plurality of threads 24 as the vial 12 passes through the vial engagement assembly 30.

FIG. 11C is a top view of the vial engagement assembly 30 once the support housing 142 is fully engaged with the main housing 140 and held in a fixed position by the snap joints 148. As shown in FIG. 11C, the vial engagement assembly 30 further includes a moveable thread 150. The moveable thread 150 includes a thread portion 152. The moveable thread 150 is connected to the thread disengagement pushbutton 44 so that when the thread disengagement pushbutton 44 is pushed in, as shown in FIGS. 11A and 11B, the moveable thread 150 is pushed outside of the radius D1 of the first opening 144. When the thread disengagement pushbutton 44 is released, springs (not shown) inside the main housing 140 force the moveable thread 150 inside of the radius D1 of the first opening 144, as shown in FIG. 11C. When the moveable thread 150 is forced inside the radius D1, the thread portion 152 is forced inside the radius D2 where it can threadily engage the plurality of threads 24 of the vial 12. In this way, the vial engagement assembly 30 is configured to selectively engage the plurality of threads 24.

FIG. 12 is a schematic cross-sectional view further illustrating the system 10 of FIG. 1 and a method for aseptic storage and delivery of biological material, according to embodiments of the disclosure. FIG. 12 shows the system 10 including a portion of the vial 12 including the vial output port 20, and a portion of the delivery device 14 including the inner funnel 48, the receiving end 34 of the tubular barrel 26 and the outer funnel 50. The vial engagement assembly 30 has been omitted for clarity. A portion of the outer funnel 50 is projecting from the receiving end 34 and the tines 106 of the dispersion funnel retaining device 104 are disposed within the dispersion funnel retaining slots 88 so that the dispersion funnel assembly 32 can be prevented from moving toward the dispensing end 36 (FIG. 1) of the tubular barrel 26, as described above in reference to FIG. 7. The vial 12 contains biological material C made of clumps of cells, as described above. The clumped biological material C needs to be broken up into individual cells, or dispersed, before being delivered to the patient. The biological material C was aseptically prepared and frozen in the vial 12 for transport and storage as described above in reference to FIG. 2 and then thawed for use. In some embodiments, thawing can include placing the vial 12 in a warm water bath. The vial 12 can then be connected to the delivery device 14 as shown in FIG. 12. The vial 12 can be connected to the inner funnel 48 by connecting the vial output port 20 to the funnel input port 60, as describe above in reference to FIG. 6. In some embodiments, a third O-ring 154 can be disposed around and between the vial output port 20 and the funnel input port 60, as shown in FIG. 12. The compressible seal 52 can then be attached to the inner funnel 48 (if not already attached), as described above in reference to FIG. 5A, and then the inner funnel 48 can be inserted into the outer funnel 50. FIG. 12 shows the system 10 just as the inner funnel 48 is being inserted into the outer funnel 50 and as the at least one projection 62 (not visible in FIG. 12) is being aligned to at least one slot 82 to align the first plurality of openings 74 with the second plurality of openings 98. During the steps described immediately above, the biological material C and any liquid present is prevented from passing through the vial output port 20, which is a pressure activated output port, as described above in reference to FIG. 2. In this way, the vial 12 can be connected to the delivery device 14.

FIG. 13 is another schematic cross-section further illustrating the system 10 of FIG. 12 and the method for aseptic storage and delivery of biological material, according to embodiments of the disclosure. FIG. 13 shows the system 10 after the vial 12 and the connected inner funnel 48 have been moved through the outer funnel 50 until the cantilevered lugs 64 engage the first recesses 84 to place the dispersion funnel assembly 32 in the open configuration, as described above in reference to FIG. 5A.

Once in the open configuration, the biological material C can be dispersed by applying a pressurized flow of liquid F to the vial input port 18 (FIG. 1) to cause the vial output port 20 to open, and the biological material C to flow out of the vial 12 and into the inner funnel 48. Individual cells of the biological material C can pass through the first plurality of openings 74, carried by the flow of liquid F, while cell clumps of the biological material C are too large to pass through the first plurality of openings 74. As the flow of liquid F continues to move through the dispersion funnel assembly 32, the flow of liquid F erodes the clumps of biological material C, breaking the clumps down into their constituent cells, which can then move through the first plurality of openings 74 and into the outer funnel 50, and then through the second plurality of openings 98 and into the tubular barrel 26. The flow of liquid F continues through the filter assembly 28 which is selected to be in the open state in which the filter medium 134 prevents the biological material C from passing through the filter assembly 28 but permits liquid to pass through the filter assembly 28, as describe above in reference to FIGS. 8-10. In this way, the biological material C can be dispersed within the delivery device 14.

Leakage of the flow of liquid F is prevented by the first O-ring 70 between the inner funnel 48 and the outer funnel 50, the second O-ring 92 between the outer funnel 50 and the tubular barrel 26, and the third O-ring 154 disposed around and between the vial output port 20 and the funnel input port 60.

Figure 13:
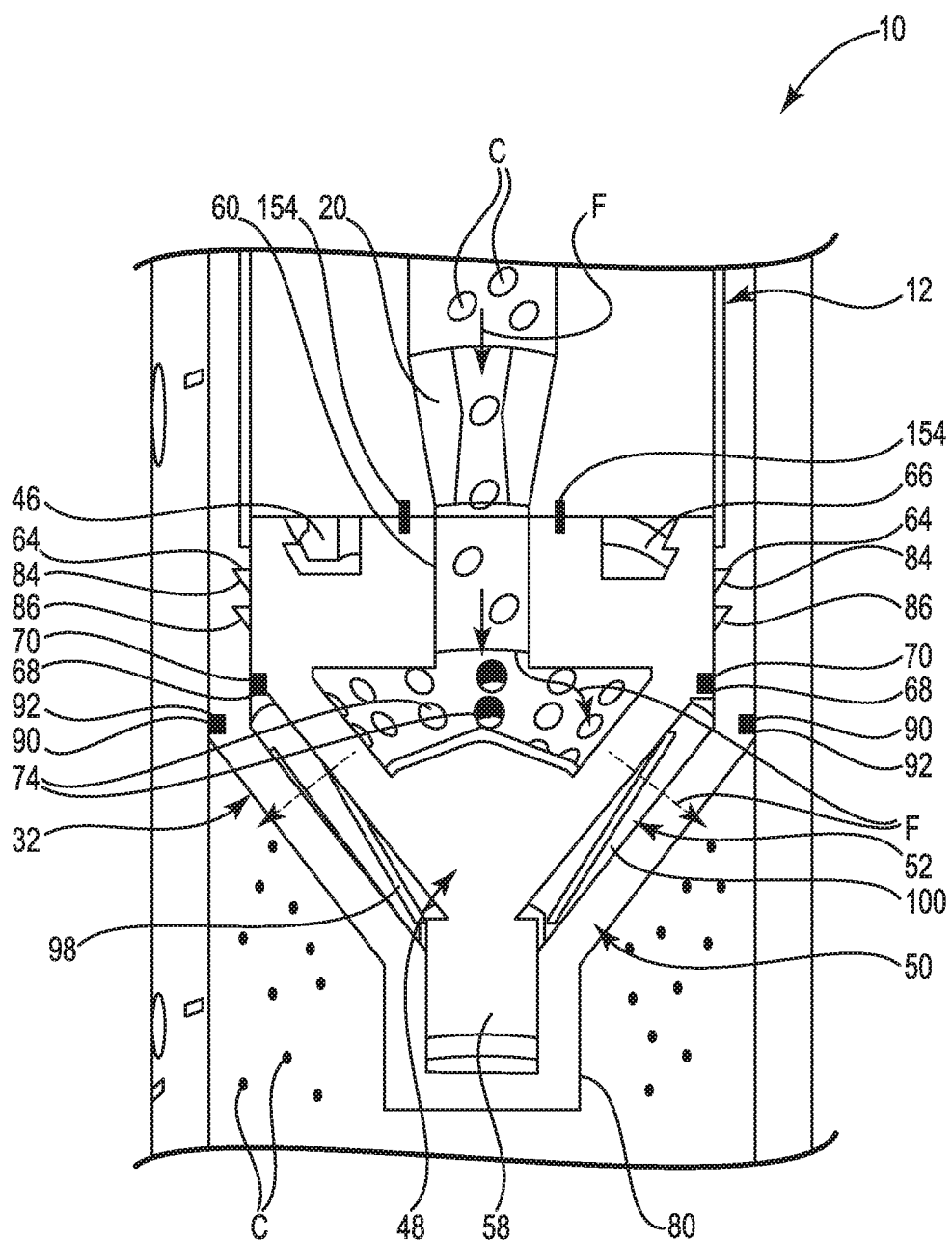
FIG. 13 is another schematic cross-section further illustrating the system of FIG. 12 and the method for aseptic storage and delivery of biological material, according to embodiments of the disclosure.
Figure 14:
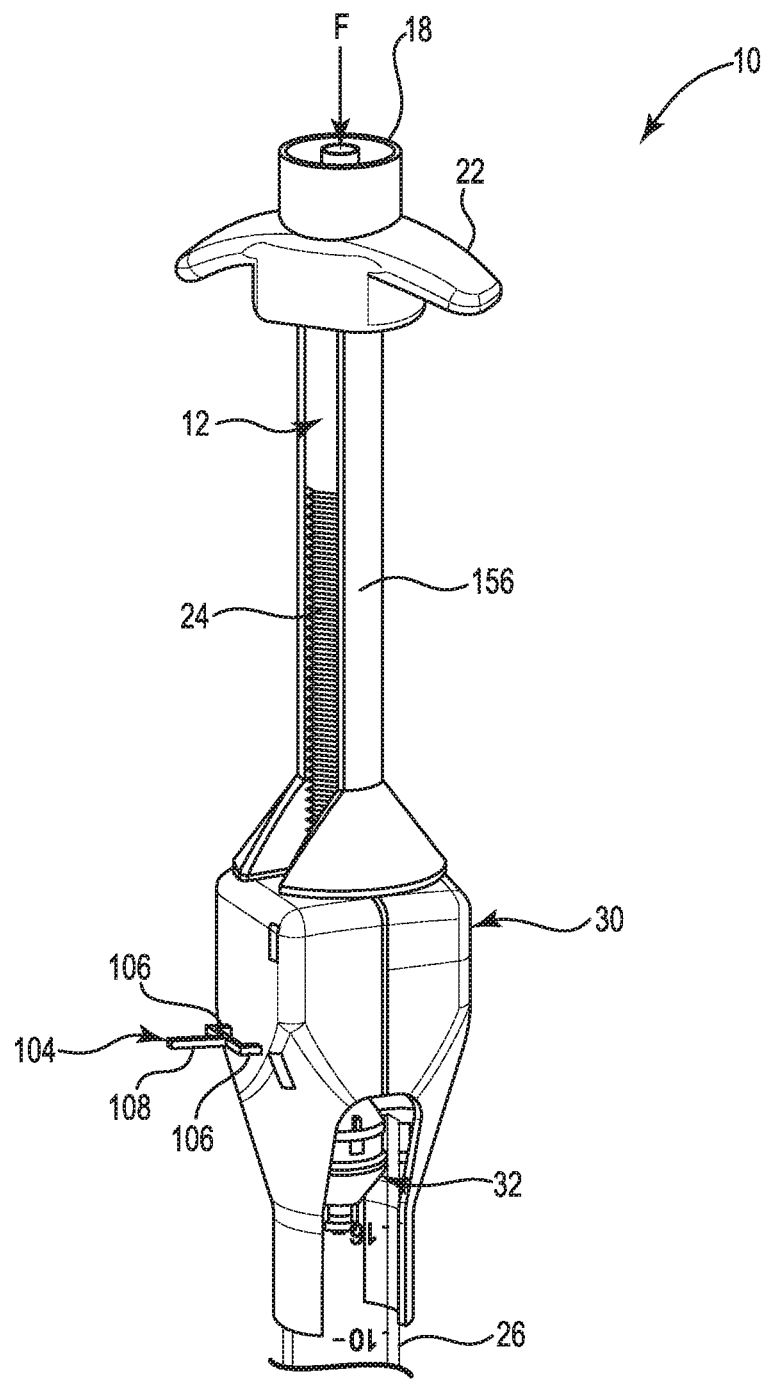
FIG. 14 is a perspective view of a portion of the system of FIG. 1, according to some embodiments.

FIG. 14 is a perspective view of a portion of the system 10 of FIG. 13, according to embodiments. FIG. 14 shows a flow of liquid F entering the vial input port 18 while the dispersion funnel retaining device 104 retains the dispersion funnel assembly 32 at the receiving end 34 of the tubular barrel 26. As shown in FIG. 14, the dispersion funnel retaining device 104 can extend through holes in the vial engagement assembly 30 so that it can be removed after the dispersion funnel assembly 32 is in the closed configuration.

During the dispersing and washing of the biological material C, the dispersion funnel assembly 32 should remain in the open configuration. As shown in FIG. 14, the delivery device 14 can further include a retaining sleeve 156. The retaining sleeve 156 fits around the vial 12 between the handle 22 and the top of the vial engagement assembly 30. The retaining sleeve 156 is relatively incompressible in the axial direction when fitted around the vial 12. The axial length of the retaining sleeve 156 is sized such that it prevents the movement the inner funnel 48 beyond the point at which the cantilevered lugs 64 engage the first recesses 84 (FIG. 13). In this way, the dispersion funnel assembly 32 remains in the open configuration until the retaining sleeve 156 is removed from around the vial 12. The retaining sleeve 156 is C-shaped in cross-section, so that it can be selectively fitted around the vial 12 and removed from around the vial 12.

Figure 15:
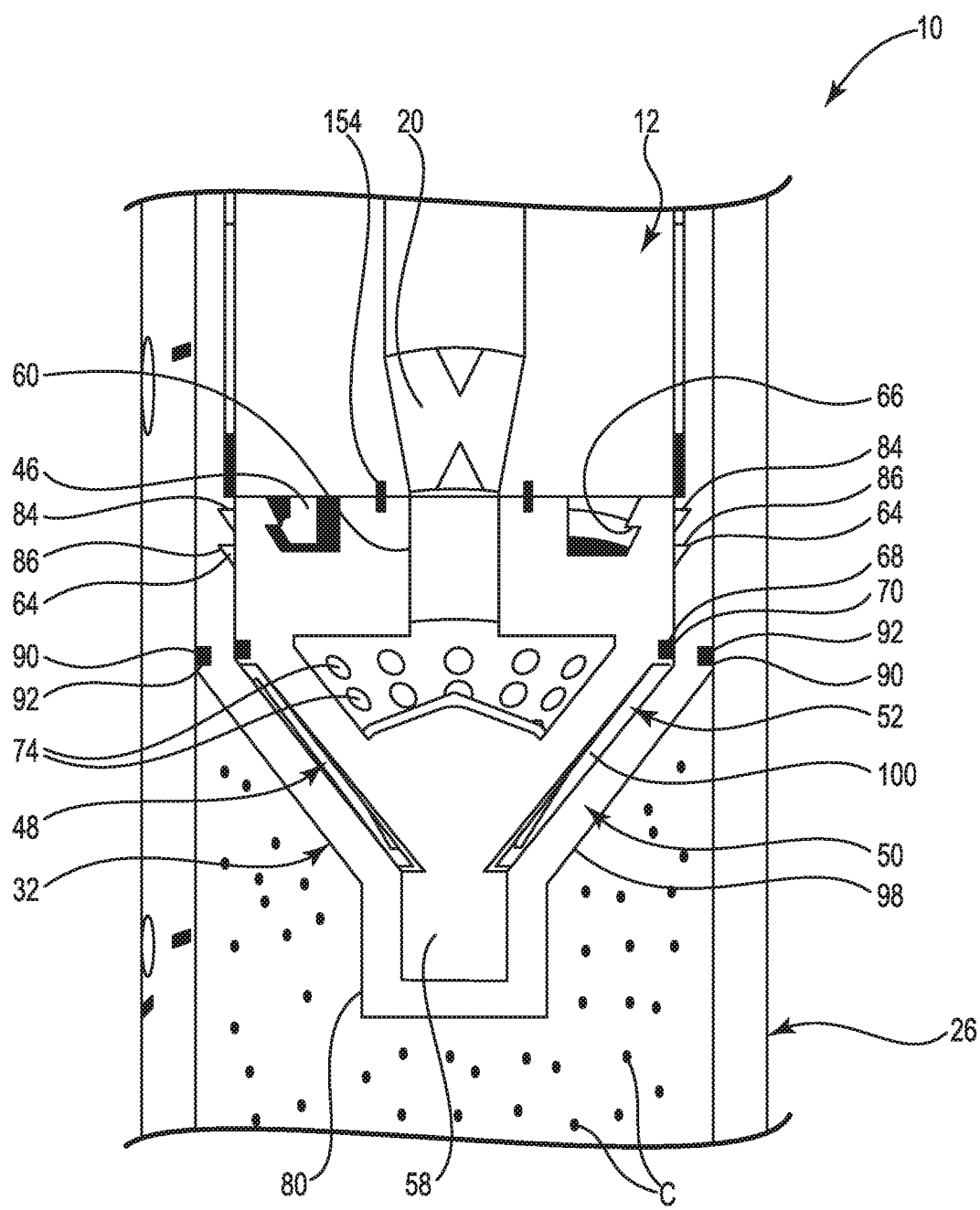
FIG. 15 is another schematic cross-section further illustrating the system of FIG. 13 and the method for aseptic storage and delivery of biological material, according to embodiments of the disclosure.

FIG. 15 is another schematic cross-section further illustrating the system 10 of FIG. 13 and the method for aseptic storage and delivery of biological material, according to embodiments of the disclosure. FIG. 15 shows the system 10 after the pressurized flow of liquid F is no longer applied to the vial input port 18, so that the vial output port 20 is closed. FIG. 15 also shows the system 10 after the vial 12 and the connected inner funnel 48 have been moved through the outer funnel 50 to disengage the cantilevered lugs 64 from the first recesses 84 and to then engaging the cantilevered lugs 64 with the second recesses 86. Moving the inner funnel 48 in this way compresses the compressible seal 52 between the inner funnel 48 and outer funnel 50 to force the compressible seal 52 to close and place the dispersion funnel assembly 32 in the closed configuration, as described above in reference to FIG. 5B.

Once in the closed configuration, the filter assembly 28 can be selected to be in the bypass state in which the biological material C can bypass the filter medium 134 and pass through the filter assembly 28 to deliver the biological material C, as described above in reference to FIGS. 8-10. The dispersion funnel retaining device 104 can be disengaged by pulling on the handle 108 to remove the tines 106 from the dispersion funnel retaining slots 88 at the receiving end 34 of the tubular barrel 26 so that the dispersion funnel assembly 32 can be moved toward the dispensing end 36 of the tubular barrel 26, as described above in reference to FIG. 7. The vial 12 can then be moved to force the connected dispersion funnel assembly 32 to slide along the tubular barrel 26, acting like a plunger in a syringe. As it moves toward the dispensing end 36, the dispersion funnel assembly 32 forces the dispersed biological material C through the filter assembly 28 and into an intravascular device connected to the bypass output port 42 (FIG. 1) for delivery to the patient.

The vial 12 can be moved in a precise fashion by rotating the vial 12 to screw the vial 12 into or out of the delivery device 14 as the plurality of threads 24 threadily engage the vial engagement assembly 30. Alternatively, the thread disengagement pushbutton 44 can be pressed (as shown in FIG. 1) to disengage the vial engagement assembly 30 from the plurality of threads 24 as described above in reference to FIGS. 11A-11C, permitting the vial 12 to be moved through the tubular barrel 26 by pushing or pulling on the vial 12, as one would with a syringe, without requiring rotation of the vial 12.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A device for aseptic delivery of biological material from a vial, the device comprising:
   a tubular barrel including a receiving end to accept a portion of the vial within the tubular barrel, and a dispensing end opposite the receiving end;
   a filter assembly fluidly connected to the dispensing end of the tubular barrel; and
   a dispersion funnel assembly configured to connect to the vial and to be at least partially disposed within the tubular barrel, the dispersion funnel assembly having an open configuration to disperse the biological material from the vial into the tubular barrel between the dispersion funnel assembly and the filter assembly, and a closed configuration to force the dispersed biological material through the filter assembly when the dispersion funnel assembly is moved toward the dispensing end of the tubular barrel,
   wherein the filter assembly includes a filter medium, the filter assembly selectable between an open state wherein the filter medium prevents the biological material from passing through the filter assembly but permits liquid to pass through the filter assembly, a bypass state wherein the biological material can pass through the filter assembly to deliver the biological material, and, optionally, a closed state wherein no liquid or biological material can pass through the filter assembly.

2. The device of claim 1, wherein the filter assembly is only selectable from the closed state to the open state and from the open state to the bypass state.

3. The device of claim 1, wherein the filter assembly further includes:
   a first output port in fluid communication with the dispensing end of the tubular barrel when the filter assembly is in the open state; and
   a second output port in fluid communication with the dispensing end of the tubular barrel when the filter assembly is in the bypass state.

4. The device of claim 1, wherein the dispersion funnel assembly includes:

an inner funnel including a first plurality of openings through the inner funnel;

an outer funnel including a second plurality of openings through the outer funnel, the inner funnel coaxial with and nested within the outer funnel such that the first plurality of openings are aligned with the second plurality of openings; and a compressible seal disposed between the inner funnel and the outer funnel, wherein in the open configuration, the compressible seal permits a fluid connection between the inner funnel and the outer funnel, and in the closed configuration, the compressible seal is compressed between the inner funnel and the outer funnel to prevent the fluid connection between the inner funnel and the outer funnel.

5. The device of claim 4, wherein:

the inner funnel further includes:

a first tubular portion; and a first conical portion coaxial with and projecting away from the first tubular portion, the first conical portion defining a first opening angle and the first plurality of openings; and the outer funnel further includes:

a second tubular portion; and a second conical portion coaxial with and projecting away from the second tubular portion, the second conical portion defining a second opening angle and the second plurality of openings, the second opening angle substantially equal to the first opening angle.

6. The device of claim 4, further including a dispersion funnel retaining device configured to engage a portion of the outer funnel extending from the receiving end of the tubular barrel to prevent the dispersion funnel assembly from being moved toward the dispensing end of the tubular barrel until the dispersion funnel assembly is in the closed configuration.

7. The device of claim 1, further including a vial engagement assembly connected to the tubular barrel at the receiving end, the vial engagement assembly configured to selectively engage a plurality of threads along a portion of a length of the vial.

8. A system for aseptic storage and delivery of biological material, the system comprising:

a vial including a tubular body to contain the biological material until delivery;

a vial input port; and a pressure activated vial output port; and a delivery device configured to connect to the vial to deliver the biological material, the delivery device including:

a tubular barrel including a receiving end to accept at least a portion of the vial including the output port within the tubular barrel, and a dispensing end opposite the receiving end;

a filter assembly fluidly connected to the dispensing end of the tubular barrel, wherein the filter assembly includes a filter medium, the filter assembly selectable between an open state wherein the filter medium prevents the biological material from passing through the filter assembly but permits liquid to pass through the filter assembly, a bypass state wherein the biological material can pass through the filter assembly to deliver the biological material, and optionally, a closed state wherein no liquid or biological material can pass through the filter assembly; and a dispersion funnel assembly configured to connect to the vial output port, the dispersion funnel assembly configured to be disposed at least partially within the tubular barrel, the dispersion funnel assembly having an open configuration to disperse the biological material from the vial into the tubular barrel between the dispersion funnel assembly and the filter assembly, and a closed configuration to force the dispersed biological material through the filter assembly when the dispersion funnel assembly is moved toward the dispensing end of the tubular barrel.

9. The system of claim 8, wherein the dispersion funnel assembly includes:

an inner funnel including a first plurality of openings through the inner funnel;

an outer funnel including a second plurality of openings through the outer funnel, the inner funnel coaxial with and nested within the outer funnel such that the first plurality of openings are aligned with the second plurality of openings; and a compressible seal disposed between the inner funnel and the outer funnel, wherein in the open configuration, the compressible seal permits a fluid connection between the inner funnel and the outer funnel, and in the closed configuration, the compressible seal is compressed between the inner funnel and the outer funnel to prevent the fluid connection between the inner funnel and the outer funnel.

10. The system of claim 9, wherein:

the inner funnel further includes:

a first tubular portion; and a first conical portion coaxial with and projecting away from the first tubular portion, the first conical portion defining a first opening angle and the first plurality of openings; and the outer funnel further includes:

a second tubular portion; and a second conical portion coaxial with and projecting away from the second tubular portion, the second conical portion defining a second opening angle and the second plurality of openings through the second conical portion, the second opening angle substantially equal to the first opening angle.

11. The system of claim 9, wherein the delivery device further includes a dispersion funnel retaining device configured to engage a portion of the outer funnel extending from the receiving end of the tubular barrel to prevent the dispersion funnel assembly from being moved toward the dispensing end of the tubular barrel until the dispersion funnel assembly is in the closed configuration.

12. The system of claim 8, wherein a portion of a length of the tubular body of the vial includes a plurality of threads, and the delivery device further includes a vial engagement assembly connected to the tubular barrel at the receiving end, the vial engagement assembly configured to selectively engage the plurality of threads.

* * * * *